(12) United States Patent
Niver et al.

(10) Patent No.: US 12,262,886 B2
(45) Date of Patent: *Apr. 1, 2025

(54) ORTHOPEDIC STABILIZATION DEVICE, KIT, AND METHOD

(71) Applicant: Medline Industries, LP, Northfield, IL (US)

(72) Inventors: Ryan Niver, Glenview, IL (US); Wesley Lloyd Reed, Libertyville, IL (US)

(73) Assignee: Medline Industries, LP, Northfield, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/408,080

(22) Filed: Jan. 9, 2024

(65) Prior Publication Data

US 2024/0148373 A1 May 9, 2024

Related U.S. Application Data

(60) Continuation of application No. 17/873,784, filed on Jul. 26, 2022, now Pat. No. 11,896,211, which is a division of application No. 16/567,983, filed on Sep. 11, 2019, now Pat. No. 11,426,154.

(51) Int. Cl.
*A61B 17/80* (2006.01)
*A61B 17/04* (2006.01)
*A61B 17/84* (2006.01)

(52) U.S. Cl.
CPC ...... *A61B 17/0401* (2013.01); *A61B 17/8042* (2013.01); *A61B 17/8057* (2013.01); *A61B 17/842* (2013.01); *A61B 2017/0404* (2013.01); *A61B 2017/0414* (2013.01); *A61B 2017/0458* (2013.01)

(58) Field of Classification Search
CPC .............. A61B 17/0401; A61B 17/842; A61B 2017/0417
See application file for complete search history.

(56) References Cited

U.S. PATENT DOCUMENTS

| 4,750,492 | A | * | 6/1988 | Jacobs | ............... | A61B 17/0487 606/232 |
| 5,306,301 | A | * | 4/1994 | Graf | ..................... | A61F 2/0805 623/13.12 |
| 9,005,245 | B2 | * | 4/2015 | Thornes | ............. | A61B 17/0401 606/232 |
| 10,206,670 | B2 | * | 2/2019 | Thornes | ............. | A61B 17/0401 |

(Continued)

*Primary Examiner* — Nicholas W Woodall
(74) *Attorney, Agent, or Firm* — Fitch, Even, Tabin & Flannery LLP

(57) ABSTRACT

An orthopedic stabilization device is provided having a first button and a suture. The first button includes a base portion and a locking loop extending from a distal surface thereof, and a locking member slidably receiving the locking loop. At least a portion of the suture extends through the locking loop superior the locking member in the axial direction and at least a portion of the suture extends through the locking loop inferior the locking member in the axial direction such that a portion of said suture is frictionally retainable between said locking member and said locking loop when the suture is tensioned. The device may include a second button with the suture disposed between the first and second buttons such that the suture may be held in tension therebetween.

21 Claims, 17 Drawing Sheets

(56) References Cited

U.S. PATENT DOCUMENTS

| | | | |
|---|---|---|---|
| 10,349,931 B2 * | 7/2019 | Stone | A61B 17/0401 |
| 2002/0161439 A1 * | 10/2002 | Strobel | A61F 2/0805 |
| | | | 623/13.14 |
| 2008/0208252 A1 * | 8/2008 | Holmes | A61B 17/842 |
| | | | 606/232 |
| 2013/0035720 A1 | 2/2013 | Perriello | |
| 2014/0257294 A1 * | 9/2014 | Gedet | A61B 17/842 |
| | | | 606/103 |
| 2018/0008255 A1 | 1/2018 | Fallin | |

* cited by examiner

ORTHOPEDIC STABILIZATION DEVICE, KIT, AND METHOD

CROSS-REFERENCE TO RELATED APPLICATIONS

This application is a continuation of U.S. application Ser. No. 17/873,784 filed Jul. 26, 2022, now issued as U.S. Pat. No. 11,896,211, which is a division of U.S. application Ser. No. 16/567,983, filed Sep. 11, 2019, now issued as U.S. Pat. No. 11,426,154, which are each hereby incorporated by reference in their entireties.

FIELD

This disclosure relates to orthopedic stabilization devices.

BACKGROUND

Numerous implants exist for repairing damaged bones and tissue. For example, fractured bones, torn joints and ligaments may be stabilized via bone plates and bone screws. Screws may not be appropriate in all applications, however. In some indications, it has been found desirable to employ various button suture devices for stabilizing certain bones or joints. Such button suture devices typically include two buttons connected via a suture, where the buttons may be positioned on opposite sides of a bone segment with suture extending therethrough in order to stabilize the bones relative to one another to promote healing. For example, button suture devices are commonly used to stabilize the tibia and fibula to repair a tear in, or damage to, the syndesmosis.

Procedures to install such button suture devices generally involve drilling a hole through the bone segment to be stabilized, advancing one of the buttons and the suture through the hole, securing the button on a far side of the bone segments, and then tightening and knotting the suture to hold the bone segments in tension. Such knotted assemblies may lose suture tension over time, and tying the knot during a surgical procedure can be burdensome. It would be desirable to provide an improved button suture device with an improved locking mechanism to maintain tension.

It has now been found that a locking device may be used as part of an orthopedic stabilizing device, as described in more detail below.

Figure 1:
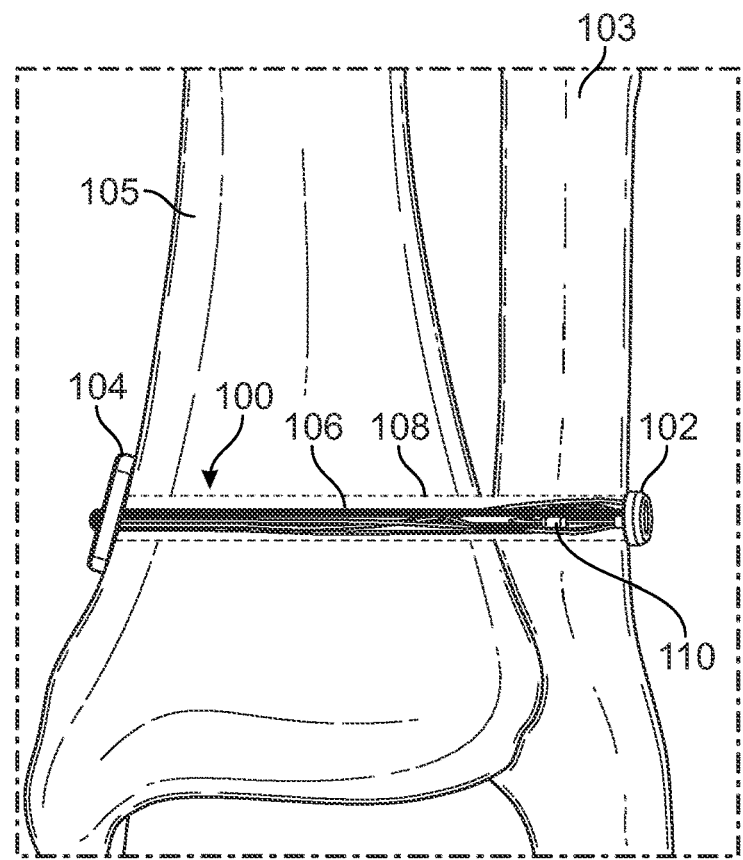
FIG. 1 is a side elevational view of a surgical site showing an exemplary orthopedic stabilization device, the device including a first button, a second button, and a suture.

Terms of orientation are for convenient reference to the drawings and are not intended to limit the orientation of the implant in use.

DETAILED DESCRIPTION

Generally, an orthopedic stabilization device is provided. The device has a first button and a suture. The first button includes a base portion and a locking loop extending from a distal surface thereof, and a locking member slidably receiving the locking loop. Generally at least a portion of the suture extends through the locking loop superior the locking member in the axial direction and at least a portion of the suture extends through the locking loop inferior the locking member in the axial direction such that a portion of said suture is frictionally retainable between said locking member and said locking loop when the suture is tensioned. The device may include a second button with the suture disposed between the first and second buttons. Via this arrangement, tension in the suture is maintained such the first button is mechanically tied to the second button or to a distal structure engaging the suture to thereby mechanically tie one or more bone segments together. The bone segments are thereby inhibited from separating, as is desirable in stabilization of the syndesmotic region between tibia and fibula and in other surgical applications.

The suture may include one or more loops or bights that extend around portions of the first and second buttons and a portion that extends around the locking member. The suture is inhibited from loosening via the frictional retainment of the suture between the locking member and the locking loop.

Additionally, a kit may be provided including an orthopedic stabilization device as described above, and one or more of a drill bit, a drill guide and passing device. The kit may include various other optional components including a bone plate, a bone screw, a guide wire, among others, or other permutations of these components. The bone plate optionally provided may include at least one first aperture sized to receive and seat the first button of the orthopedic stabilization device, and may further include at least one second aperture sized to receive the at least one bone screw. The bone screw may be received through the second aperture to secure the bone plate to a bone segment. Thereafter, the orthopedic stabilization device may be installed as discussed hereinafter and the first button may be seated and received at least partially in the first aperture of the bone plate.

Further, a bone stabilization method is provided. One or more bone segments may be surgically exposed and a hole may be drilled through the one or more bone segments. A second button and suture of the orthopedic stabilization device may be advanced through the hole such that the second button exits the hole at a distal end. Once the second button of the device has exited the hole and is seated adjacent the far cortex, the device may be tensioned to tie the first button to the second button, whereby the locking device frictionally retains a portion of the suture between the locking member and the locking loop thereby maintaining tension in the suture. In some forms, the stabilization device may be tensioned by applying tension to the suture proximate the first button, and in other forms the stabilization device may be tensioned by applying tension to the suture proximate the second button, as described further below.

Such a method may likewise be use in connection with a bone plate. For example, the bone plate may be positioned proximate, and fastened to, a bone segment via one or more bone screws. Thereafter, the above-described method may be employed to stabilize the bone segments via the orthopedic stabilization device.

The orthopedic stabilization device provided herein may be used in many orthopedic applications, such as stabilizing the syndesmosis between the tibia and the fibula of a patient, acromioclavicular (AC) repair, bicep tendon repair, bicep tendon reattachment, knee ligament repairs (e.g., anterior cruciate ligament (ACL) and posterior cruciate ligament (PCL) repairs), carpometacarpal (CMC) repair in the hand, among others. It is also contemplated that the orthopedic stabilization device can be used in non-orthopedic applications. In some forms, the second button of the orthopedic stabilization device may be omitted such that the suture may alternatively be attached or coupled to tissue (e.g., a tendon, a ligament, a bone, etc.) or another device (e.g., a screw or anchor) and the device may thereafter be tensioned.

Referring now to FIG. 1, the exemplary orthopedic stabilization device 100 includes a first button 102, a second button 104, and a suture 106 held in tension. The suture mechanically ties the first button 102 to the second button 104 and thereby inhibits separation of the tibia 103 and fibula 105. The device is shown extending through the fibula 103 and tibia 105 of a patient's leg to stabilize the syndesmosis. As illustrated, the first button 102 is seated adjacent the lateral cortex of the fibula 103, and the second button 104 is seated adjacent the medial cortex of the tibia 105, with the suture 106 extending through a bore 108 that has been drilled though both bones 103, 105. When under tension, the suture 106 is cinched and hence frictionally retained between a locking member 110 and a locking loop 112 (also shown in FIG. 2) such that the tension between the first and second buttons 102, 104 is maintained, as described in more detail below.

The suture 106 may be manufactured out of a variety of filaments or fibers including, by way of example, polymer filaments, metallic filaments, and organic filaments. Alternatively, the suture 106 may be a suture braid having braided filaments such as high strength #5 braided suture. In other forms, the suture 106 may be formed of ultrahigh molecular weight polyethylene braided with strands of polyester, collagen, silk, nylon, among other suture materials.

Additionally, the suture 106 may be formed of different lengths depending on the surgical application. The suture 106 should be of a sufficient length that it may looped around the first button 102 and the second button 104 and around the locking member of the locking loop to provide an amount of slack to allow the device 100 to be installed in its intended application, and thereafter tensioned, in a variety of applications.

Figure 2:
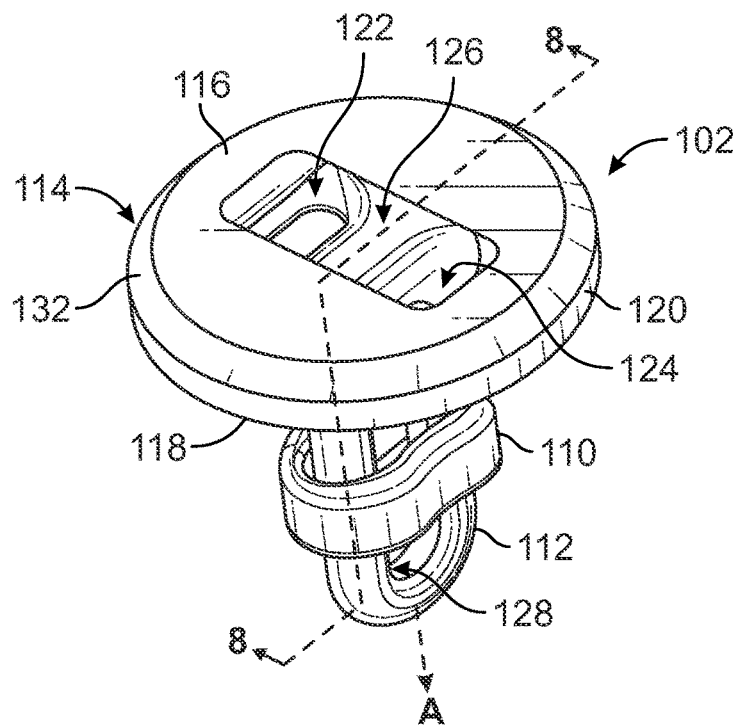
FIG. 2 is a perspective view of the first button of the orthopedic stabilization device of FIG. 1 showing a locking member slidably received over a locking loop.

As shown in FIG. 2, the first button 102 includes a base portion 114 having a proximal surface 116, a distal surface 118, and a sidewall 120 extending therebetween. As shown, the first button 102 includes a first opening 122 and a second opening 124 sized to receive a portion of suture 106, and a first intermediate area 126 extending between the first and second openings 122, 124. A locking loop 112 is provided extending axially away in the distal direction (arrow A) from the distal surface 118 of the base portion 114 and defining an opening 128. Additionally, a locking member 110 is shown disposed over the locking loop 112. The locking member 110 is sized slightly larger than the locking loop 112 such that the locking member 110 may slide along the locking loop 112. The first button 102 may be made of titanium or a titanium alloy, a stainless-steel alloy, a polyether ether ketone (PEEK) material, a poly-L-lactic acid (PLLA) material, or an alternative bioresorbable material.

Additionally, the first button 102 may include one or more chamfered or filleted surfaces, the purpose of which is to inhibit tissue irritation once the device 100 is installed in a bone segment. For example, the sidewall 120 may include a chamfered or filleted edge 132 therearound. Additionally, the first intermediate area 126 and the first and second openings 122, 124 may comprise filleted surfaces (e.g., filleted surface 134) such that the suture 106 may smoothly slide, and be tensioned around, the first intermediate area 126.

Figure 3:
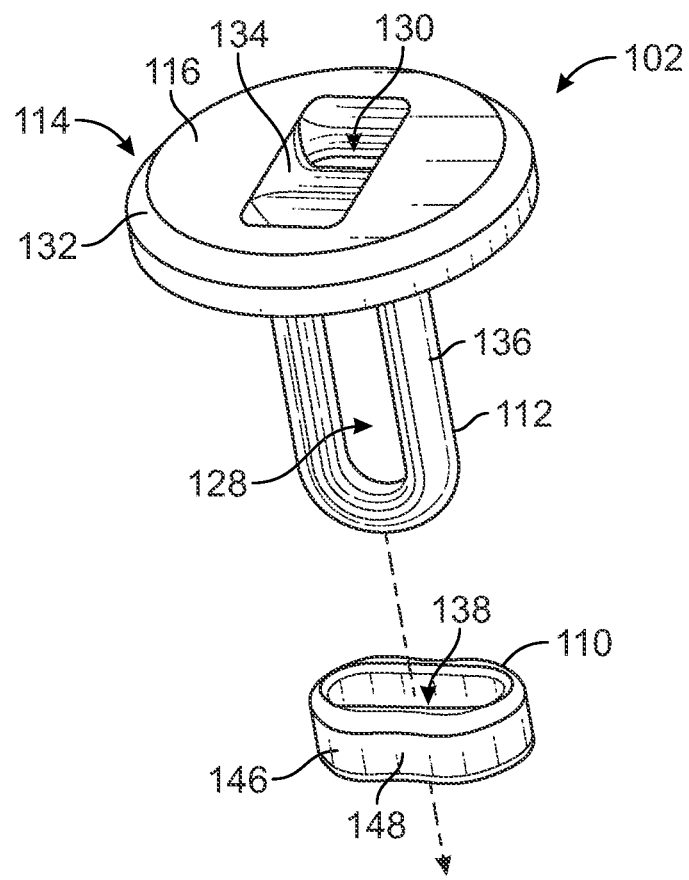
FIG. 3 is a perspective view of the first button of the orthopedic stabilization device of FIG. 1, showing the locking member separated from the locking loop.
Figure 4:
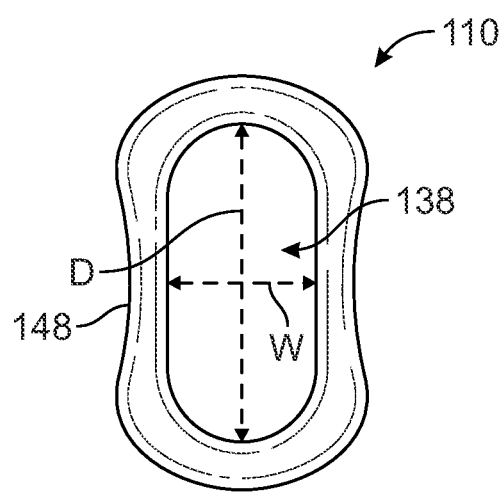
FIG. 4 is a top plan view of the locking member shown in FIG. 3.
Figure 6:
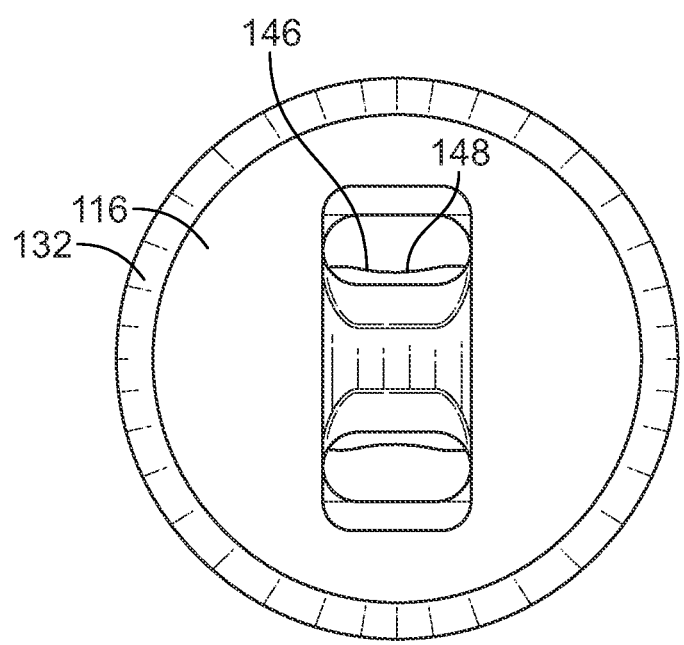
FIG. 6 is a top plan view of the first button shown in FIG. 2.
Figure 7:
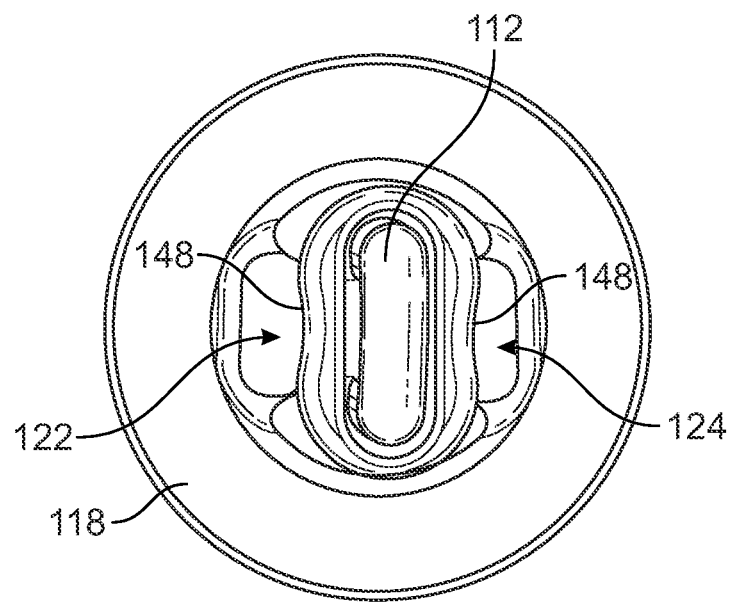
FIG. 7 is a bottom plan view of the first button shown in FIG. 2, including the locking member.
Figure 8:
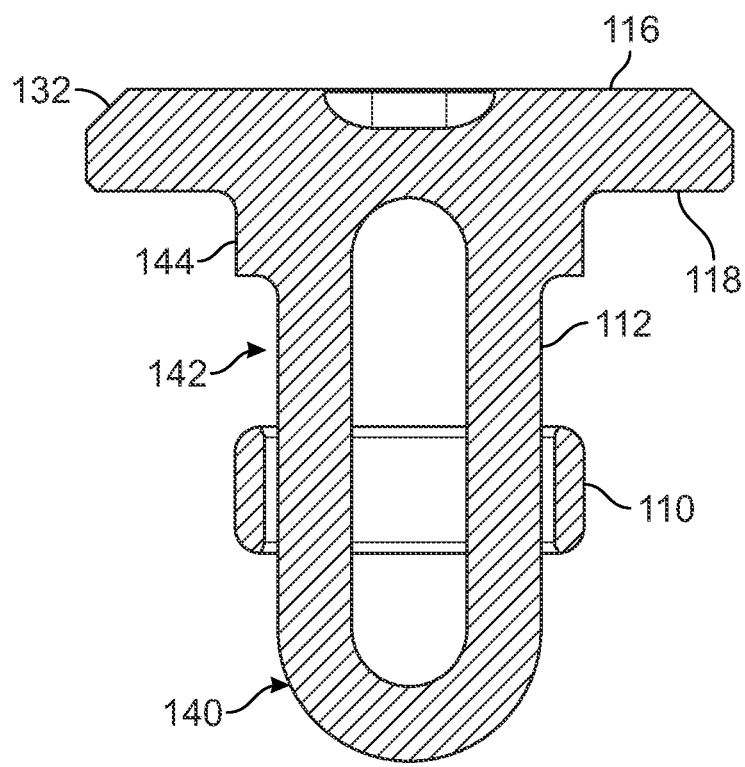
FIG. 8 is a cross-sectional view of the first button of FIG. 2 taken along line 8-8 in FIG. 2.

As shown in both FIGS. 3 and 4, the locking member 110 includes an aperture 138 therethrough sized to correspond with the shape of the locking loop 112 such that it may be slidably received thereon (as shown more clearly in FIG. 6). As illustrated, the aperture 138 has an obround shape sized to correspond with the perimeter of the locking loop 112. More particularly, the aperture 138 of the locking member 110 is sized such that there is an allowance between the outer surface 136 of the locking loop 112 and the locking member 110 sufficient to permit passage of a suture so as to frictionally retain a portion of suture 106 therebetween when tension is applied.

The allowance between the aperture 138 of the locking member 110 and surface 136 the locking loop 112 is less than the thickness of the suture 106 such that the locking member 110 is inhibited from sliding off of the locking loop 112 over the suture 106. In some forms, the aperture 138 of the locking member 110 is defined by a width W and a depth D, wherein the width W of the aperture 138 is a maximum of between about 1 to 15%, or in some cases about 1 to 3%, greater than the width of the locking loop 112 and wherein the depth D of the aperture 138 is a maximum of between about 1 to 15%, or in some cases about 1 to 3%, greater than a depth of the greatest dimension of the perimeter of locking loop 112. The allowance between the locking member 110 and the locking loop 112 may be further adjusted depending on the thickness of the suture 106 used to tie the first button 102 to the second button 104.

Figure 5:
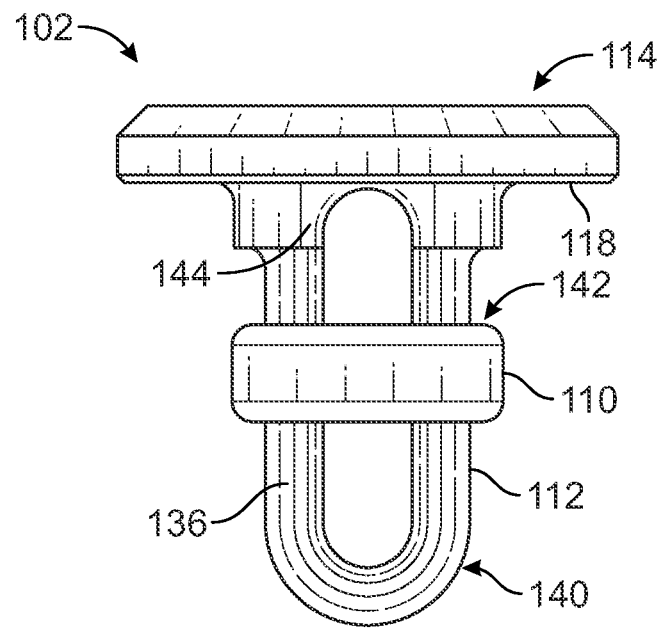
FIG. 5 is a front elevational view of the first button shown in FIG. 2, showing the locking member.

As shown in FIG. 5, the locking member 110 is positioned over the locking loop 112 such that the locking member 110 is slidably engaged therewith and may be slidably moved between a lower portion 140 of the locking loop 112 and an upper portion 142 of the locking loop 112. A flange portion 144 may be included between the base portion 114 and the locking loop 112. The flange portion 144 may be sized to be at least partially received and seated in a bone hole drilled through a portion of bone. So configured, the flange portion 144 may be seated in the bone hole to retain the device 100 relative to the bone and the distal surface 118 of the first button 102 may directly abut the cortex of a bone segment. Additionally, the flange portion 144 may provide additional structural integrity to the first button 102.

Figure 9:
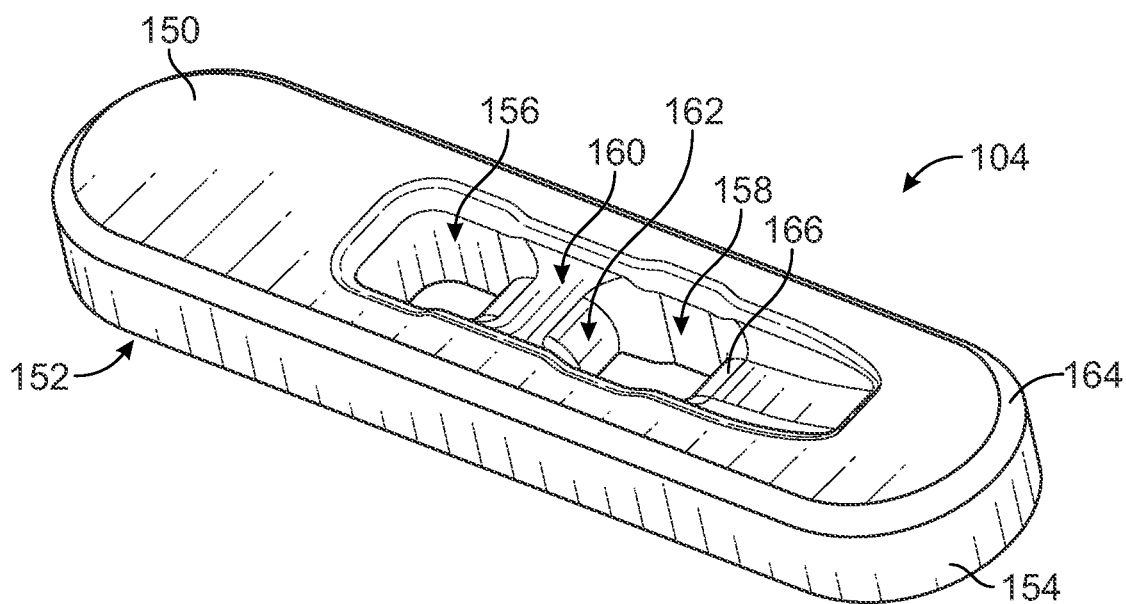
FIG. 9 is a perspective view of the second button of the orthopedic stabilization device of FIG. 1.
Figure 10:
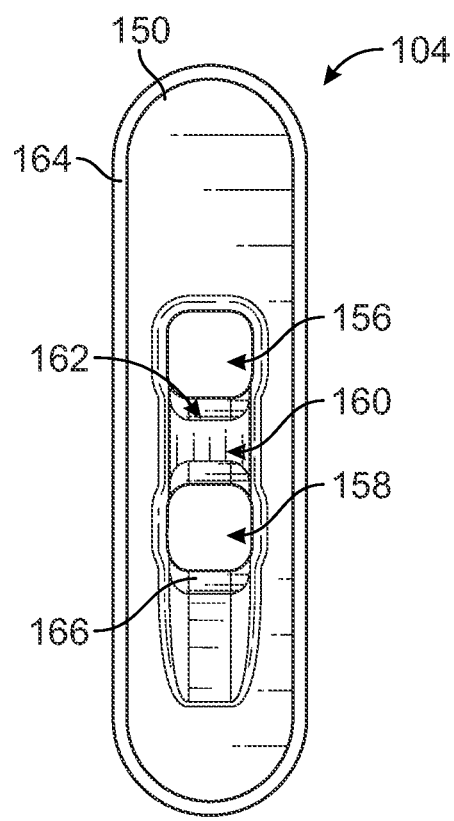
FIG. 10 is a top plan view of the second button shown in FIG. 9.

FIGS. 9 and 10 shows an exemplary second button 104 of the orthopedic stabilization device 100 having a proximate surface 150, a distal surface 152, and a sidewall 154 extending therearound. The second button 104 includes first and second openings 156, 158 sized to receive a portion of suture 106 and further includes a second intermediate area 160 extending therebetween. The first and second openings 156, 158 are sized to receive a portion of suture 106 such that a bight of the suture 106 may be looped through the openings 156, 158 and around the second intermediate area 160 to couple the second button 104 to the first button 102 when the device 100 is assembled. In some forms, the suture 106 may form multiple loops around the second intermediate area 160. As illustrated, the first and second openings 156, 158, along with the second intermediate area 160, are countersunk such that the suture 106 looping therearound is seated within a countersunk portion 162 when the device 100 is assembled. The second button 104 may be made of titanium, a stainless-steel alloy, a polyether ether ketone (PEEK) material, or a poly-L-lactic acid (PLLA) material, or an alternative bioresorbable material. The second button 104 may be formed of the same material of a different material different from that of the first button 102.

The second button 104 may likewise include one or more chamfered or filleted surfaces the purpose of which is to inhibit tissue irritation once the device 100 is installed in a bone segment. For example, the sidewall 154 may include a chamfered or filleted edge 164 therearound. Additionally, the second intermediate area 160 and the first and second openings 156, 158 of the second button 104 may comprise filleted surfaces (e.g., filleted surface 166) such that the suture 106 may smoothly slide, and be tensioned around, the second intermediate area 160.

Figure 11:
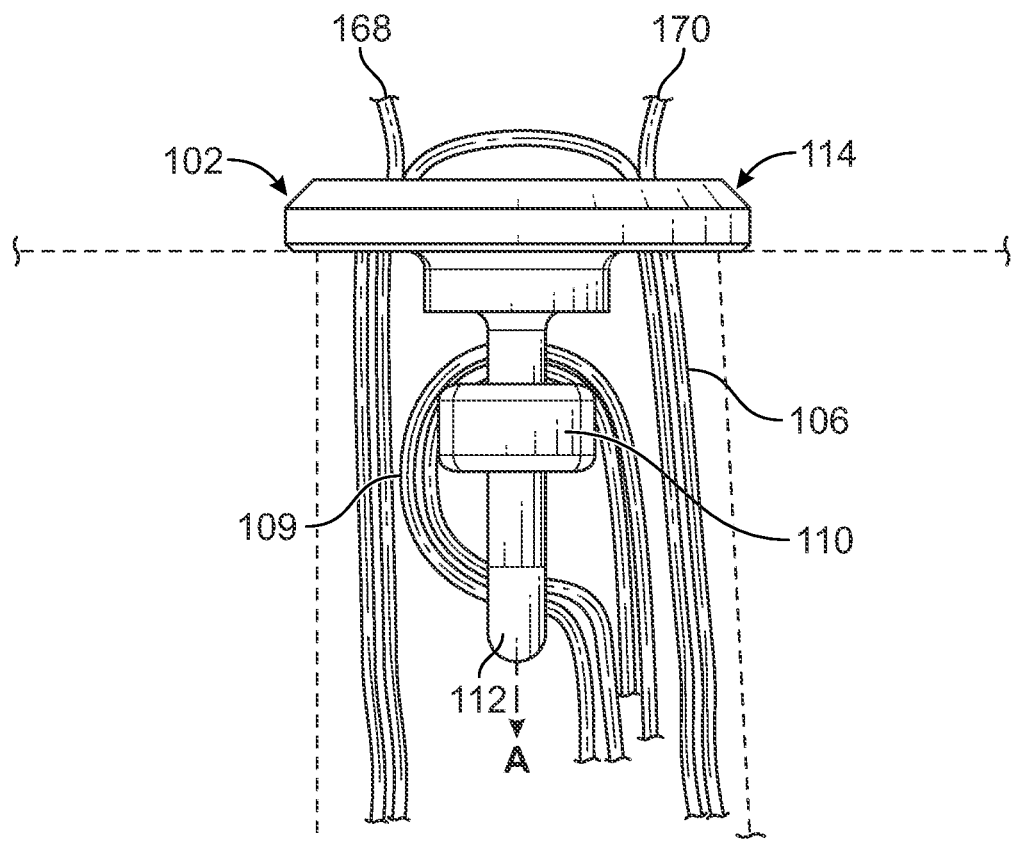
FIG. 11 is a side elevational view of the orthopedic stabilization device of FIG. 1, showing the suture in an untensioned state.

FIG. 11 shows the first button 102 seated in a portion of bone with the locking member 110 slidably received over the locking loop 112 before tension has been applied. The suture 106 is shown having a first end 168 and a second end 170 extending outwards through the first and second openings 122, 124 of the first button 102, and a bight of which extends at least once around the first intermediate area 126 of the first button 102 and a bight of which extends at least once around the second intermediate area 160 of the second button 104 (not shown in FIG. 11) thus coupling the two buttons 102, 104 to one another. Additionally, the suture 106 is shown extending through the locking loop 112 inferior the locking member 110, around the locking member 110, and through the locking loop 112 superior the locking member 110. It is seen that this forms a loop 109 around the locking member 110. Notably, this loop 109 may be formed by passing the suture around the locking member in any direction and may be formed in any suitable fashion.

Figure 12:
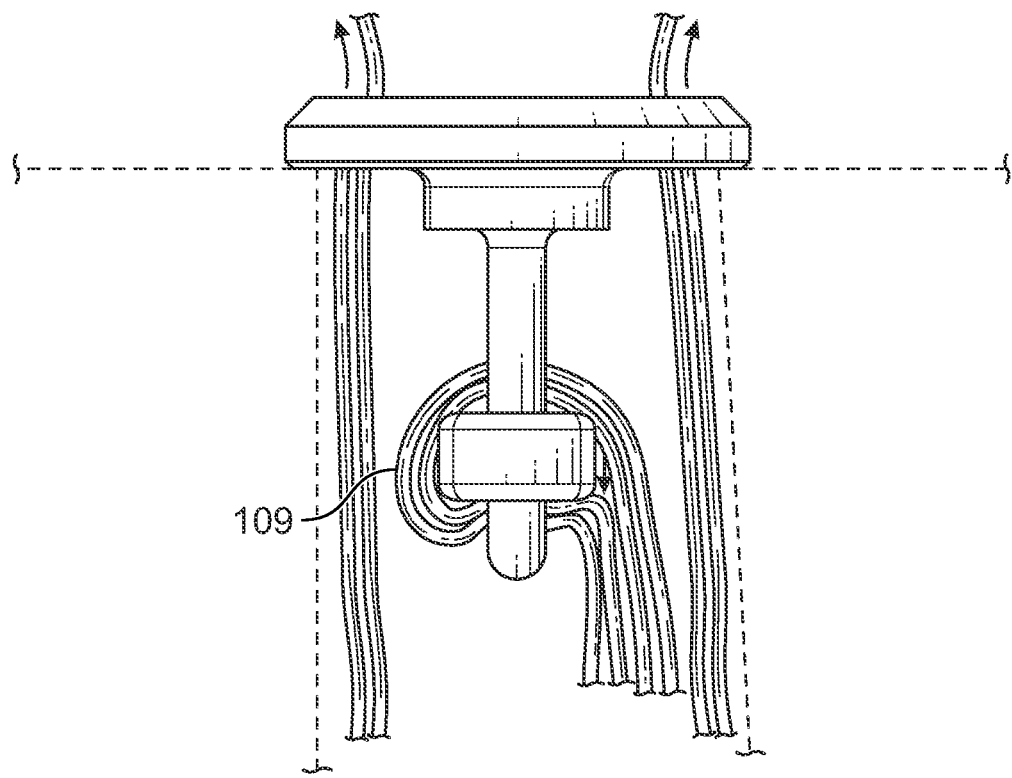
FIG. 12 is a view similar to FIG. 11 but showing the suture in a tensioned state with the suture cinched between the locking member and locking loop and the second button thereby tied to the first button by the suture.

Upon installation into one or more bone segments, tension may be applied to the first and second ends 168, 170 of the suture 106 to pull the suture 106 taut and thereby apply tension to the device 100. Once tensioned, as illustrated in FIG. 12, the loop 109 of suture 106 that extends around the locking member 110 will be biased axially away from the button 102 and will bias the locking member 110 in this direction. Because a portion of the suture extends through the locking loop 112 inferior the locking member 110, a portion of the suture 106 will be cinched and frictionally retained between the locking member 110 and the locking loop 112. This operates as a locking mechanism to inhibit the suture from losing tension. So configured, the first and second buttons 102, 104 are mechanically tied, and the locking mechanism resists separation of first and second buttons 102, 104 and hence separation of adjoining bone segments. The frictional retainment of the suture 106 provides a one-way locking mechanism such that no knotting of the suture 106 is required to maintain tension in the device 100 once installed.

Figure 13:
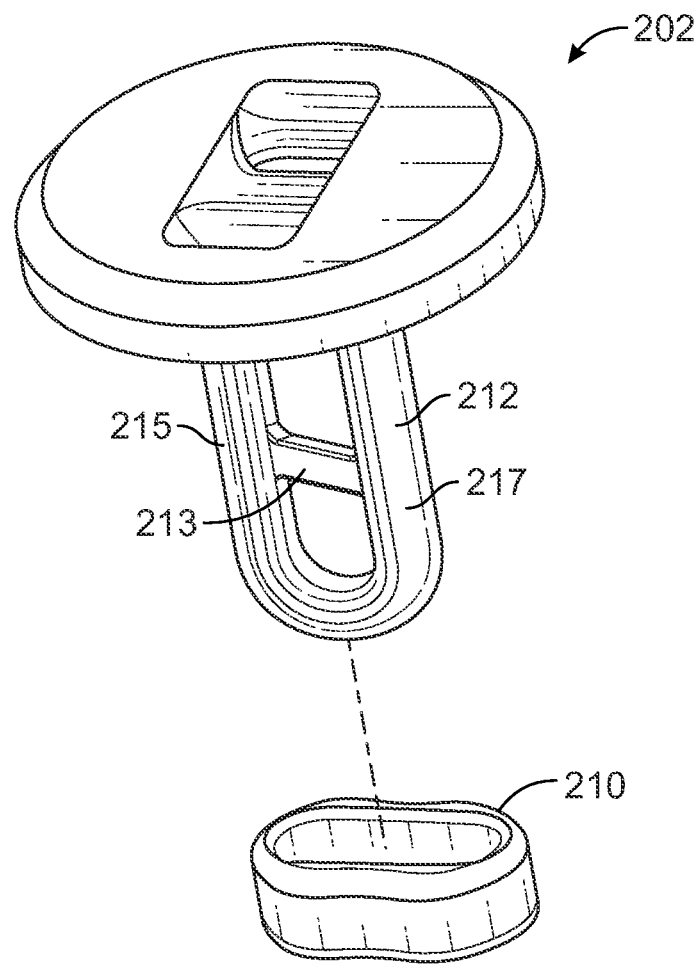
FIG. 13 is a perspective view of an alternative embodiment of the first button.

The alternative first button 202 shown in FIG. 13 includes a cross-bar 213 extending between leg portions 215, 217 of the locking loop 212. The suture 106 may extend through the locking loop 212 in various configurations (not shown) to increase the frictional engagement between the locking member 210, the locking loop 212, and the suture 106.

Figure 14A:
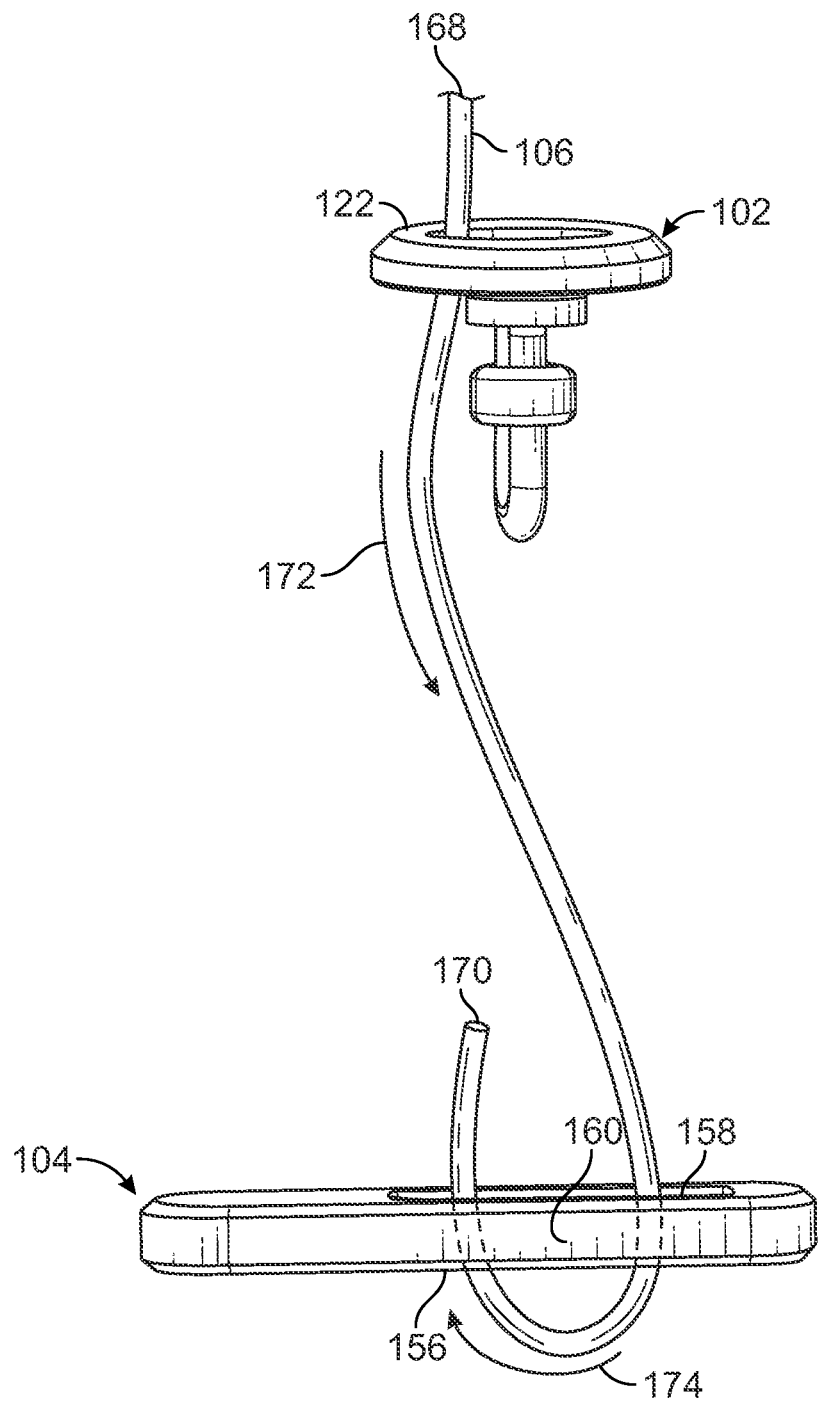
FIGS. 14A-E illustrate progressively an exemplary method of assembling the orthopedic stabilization device of FIG. 1.
Figure 14B:
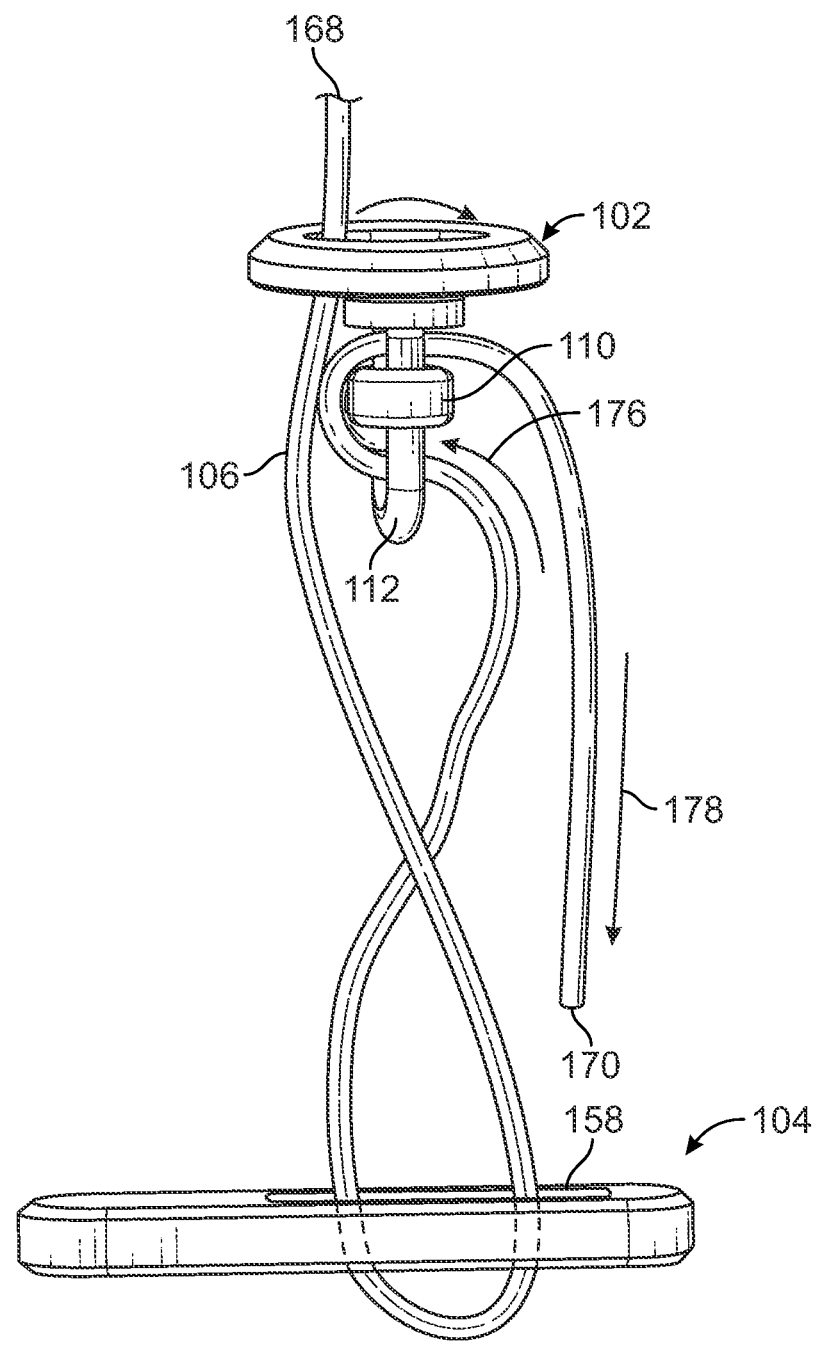
Figure 14C:
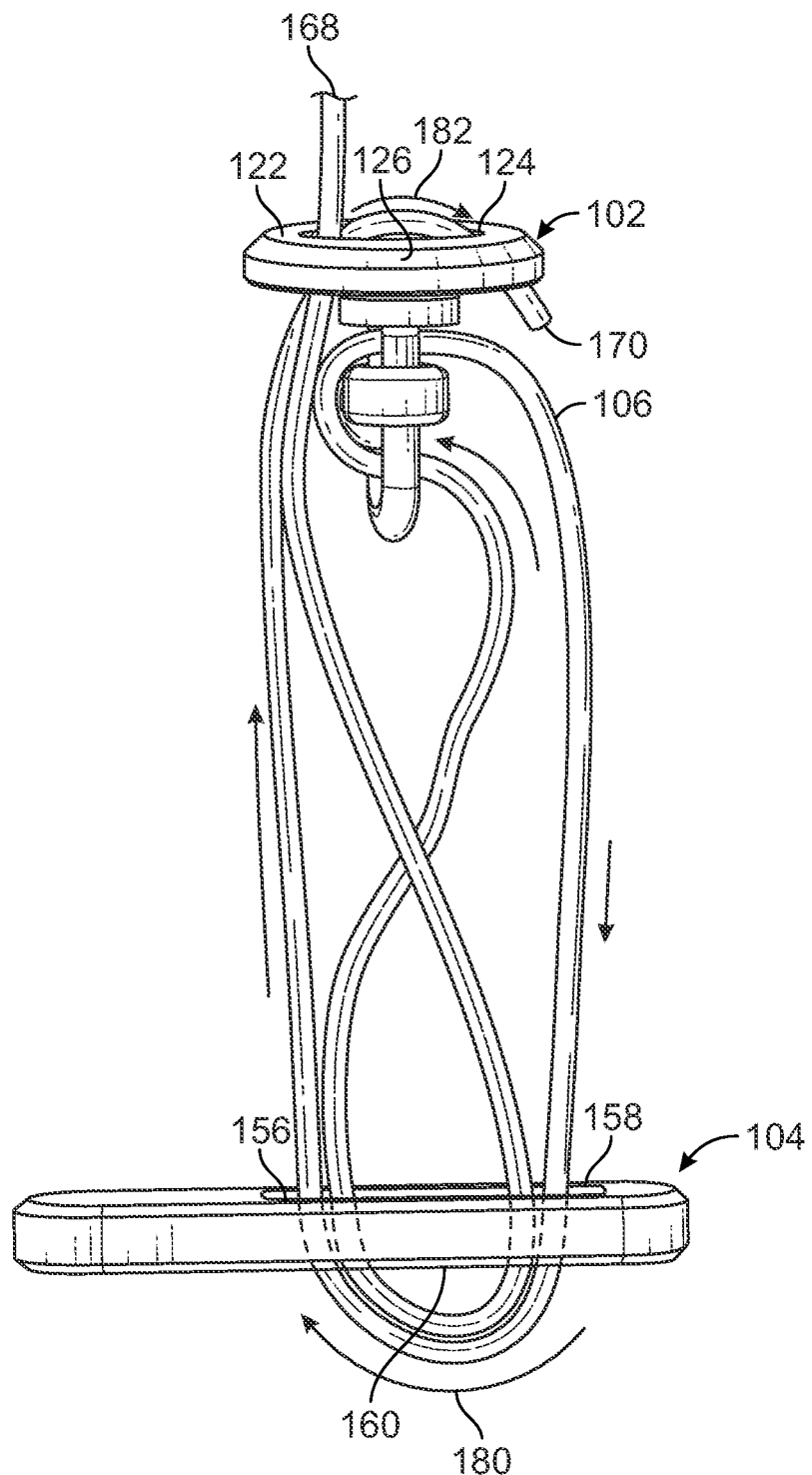

With reference to FIGS. 14A-14E, the length of suture 106 shown between the first and second buttons 102, 104 is shown only for simplicity of illustration, and the length of suture 106 or slack thereof may be adjusted during assembly depending on the length of the bone segment the orthopedic stabilization device 100 is designed to stabilize. As shown in FIG. 14A, the suture 106 having bitter end 170 may be advanced through the first opening 122 of the first button 102 at arrow 172 in an entering pass, advanced through the second opening 158 of the second button 104 at arrow 174, over the second intermediate area 160, and back through the first opening 156 of the second button 104. Continuing to FIG. 14B, the suture 106 continues to advance through the locking loop 112 inferior the locking member 110 at arrow 176, around the locking member 110, and back through the locking loop 112 and towards the second opening 158 of the second button 104 at arrow 178. In FIG. 14C, the suture 106 continues to advance through the second opening 158 of the second button 104, over the second intermediate area 160 at arrow 180, back through the first opening 156 of the second button 104, through the first opening 122 of the first button 102 through the distal side 118 thereof, over the first intermediate area 126 at arrow 182, and through the second opening 124 of the first button 102.

Figure 14D:
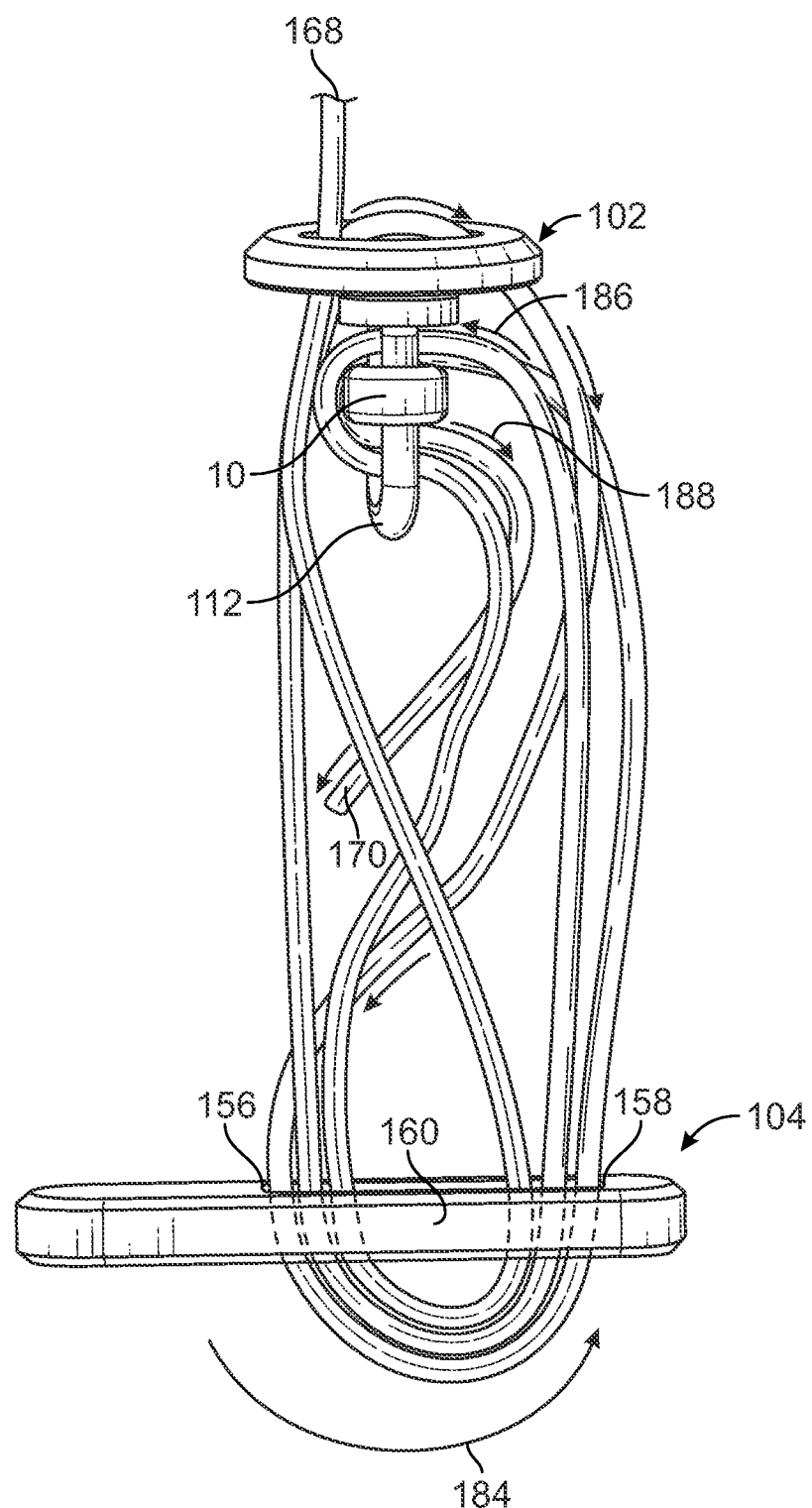
Figure 14E:
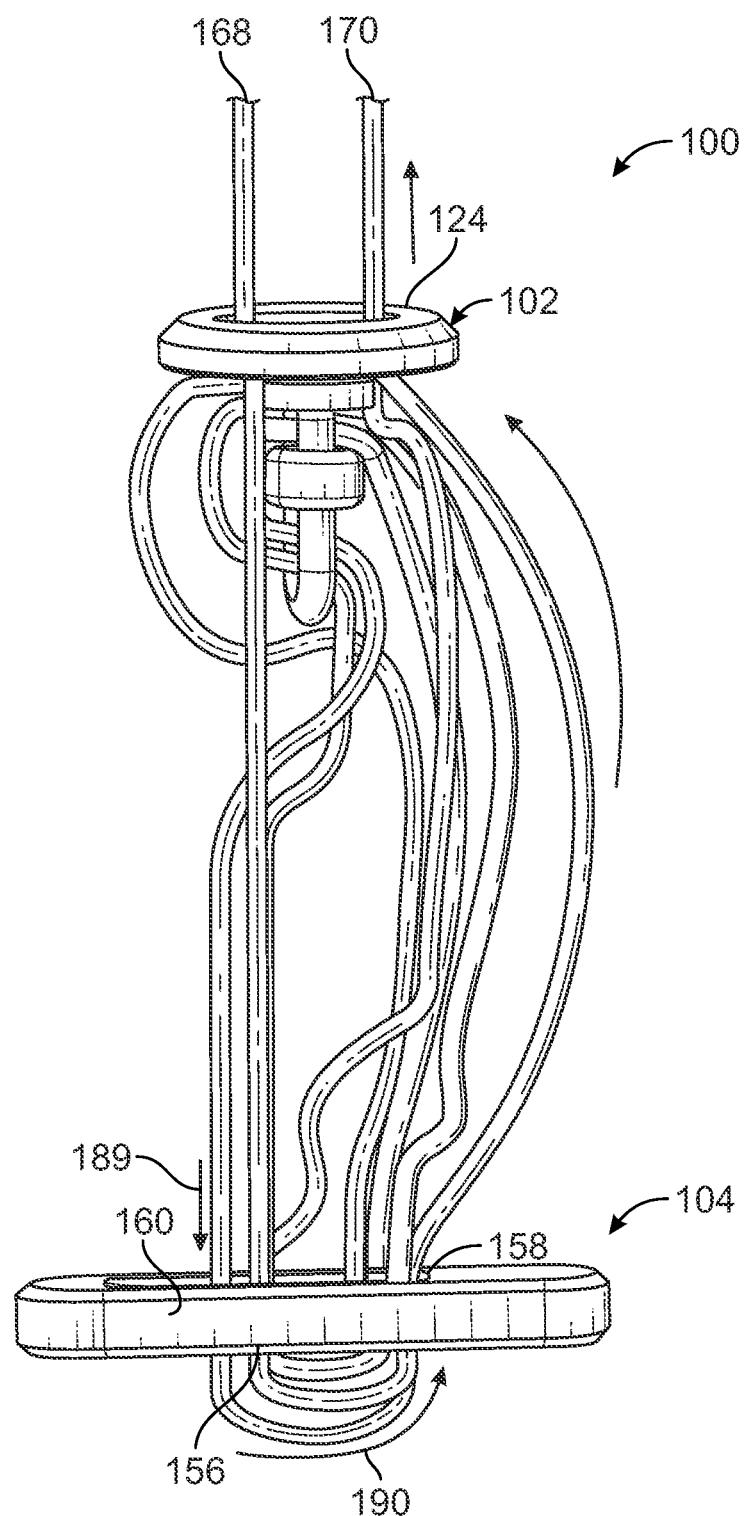

In FIG. 14D, the suture 106 is next advanced through the first opening 156 of the second button 104, around the second intermediate area 160 at arrow 184, through the second opening 158 of the second button 104, through the locking loop 112 superior the locking member 110 at arrow 186, around the locking member 110, and through the locking loop 112 inferior the locking member 110 at arrow 188. Finally, in FIG. 14E, the suture 106 is advanced through the first opening 156 (arrow 189) of the second button 104, around the second intermediate area 160 at arrow 190, and through the second opening 158 of the second button 104. The suture makes an exiting pass through the second opening 124 of the first button 102 such that the first and second ends 168, 170 of the suture 106 protrude from the proximal side 116 of the first button 102 and may thereafter be used to tension the device 100. So assembled, FIG. 14E shows the exemplary assembled orthopedic stabilization device 100 in an untensioned state. The steps illustrated above in FIGS. 14A-14E are exemplary, and the suture 106 may be threaded through the first and second buttons 102, 104 in other ways. In some forms, the second button 104 may be omitted from the above described method such that the loop typically formed therearound may be affixed or coupled to a portion of tissue (e.g., a bone, a ligament, a tendon, etc.) or a separate device (e.g., a screw, an anchoring structure, or the like).

For example, in some forms, the second button 104 may be omitted such that the suture 106 extends through the first button 102 and around the locking member 110 as described above, and terminates in a looped portion of suture 106 (not shown). So configured, the looped portion of suture 106 may be looped around tissue such as a tendon, bone, etc. to tie the first button 102 to the tissue and hold the suture 106 in tension therebetween, or may be coupled to another structure, such as a screw or anchor, such that the suture 106 may be tensioned to tie the first button 102 to the other structure provided.

Figure 15:
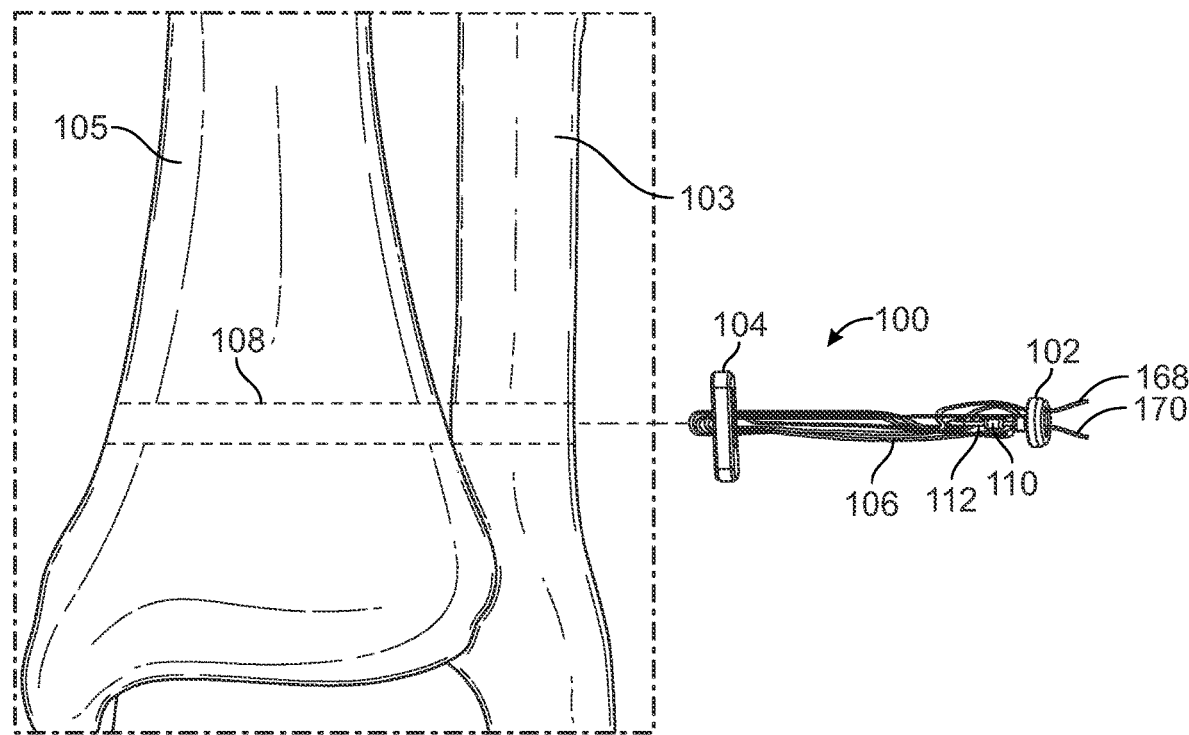
FIG. 15 is a perspective view of a surgical site showing a bore through the fibula and tibia of a patient's leg and the stabilization device of FIG. 1 positioned for placement within the bore.

With reference to FIGS. 15-18, an example method of stabilizing a bone using an orthopedic stabilization device 100 is provided. More specifically, FIGS. 15-18 provide a method of stabilizing the syndesmosis and show a tibia 105 and a fibula 103 of a patient with the syndesmosis positioned therebetween. Referring now to FIG. 15, a tibia 105 and a fibula 103 are shown after being surgically exposed and having a bore 108 drilled therethrough (i.e., a fibular tunnel and a tibia tunnel) for receiving the orthopedic stabilization device 100. To create the bore, an incision may be made on the lateral side of the patient's leg to expose a portion of the fibula 103. A surgical drill bit may then be used to bore a hole through the fibula 103 and tibia 105 to facilitate insertion and installation of the orthopedic stabilization device 100 provided herein. In other forms, a guide wire (e.g., guide wire 215 shown in FIG. 22) may be inserted through the bones prior to drilling such that a cannulated drill bit may be received on and advanced along the guide wire to drill the bore 108 through the bones. The bore 108 is sized to accommodate insertion of the second button 104 therethrough when the second button 104 is positioned in a flat configuration (shown in FIG. 16).

Figure 16:
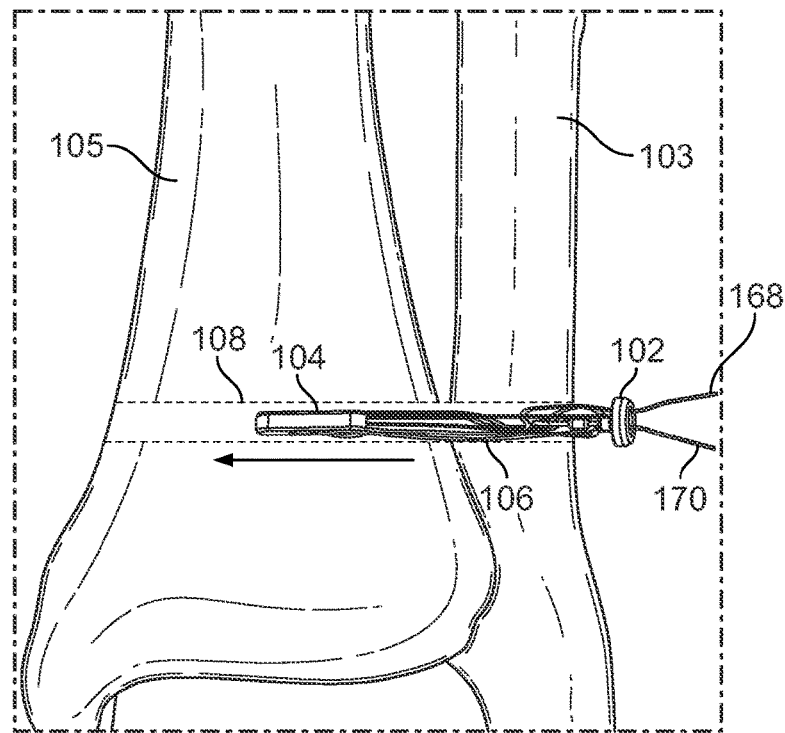
FIG. 16 is a perspective view of the surgical site of FIG. 15 showing a second button of the orthopedic stabilization device of FIG. 1 being advanced through the bone hole.

FIG. 16 shows the second button 104 of the orthopedic stabilization device 100 being advanced through the bone bore 108 drilled through the bone segments shown in FIG. 15. The second button 104 may be advanced through the bone bore 108 in the flat configuration to exit the far cortex of the tibia as shown in FIG. 16 in a variety of ways. For example, the second button 104 may be pulled through the bone hole 108 from the lateral side to the medial side using a pin or needle-like passing device 220 (shown in FIG. 22) such that the second button 104 exits the bone bore 108 proximate the medial portion of the tibia 105. For example, the passing device 220 may include a portion of suture or string coupled to the second button 104 (e.g., through the openings 156, 158) such that the needle-like passing device 220 may be advanced through the bore 108, and through the patient's skin on the medial portion of the tibia 105. Thereafter, the passing device 220 may be used to pull the second button 104 through the bore and manipulate positioning thereof against the medial portion of the tibia 105 via the suture or string coupled to the second button 104. In such forms, it may be desirable or necessary to make a small incision in the medial size of the tibia to adjust or manipulate the second button 104 once it exits the far cortex thereof.

Figure 17:
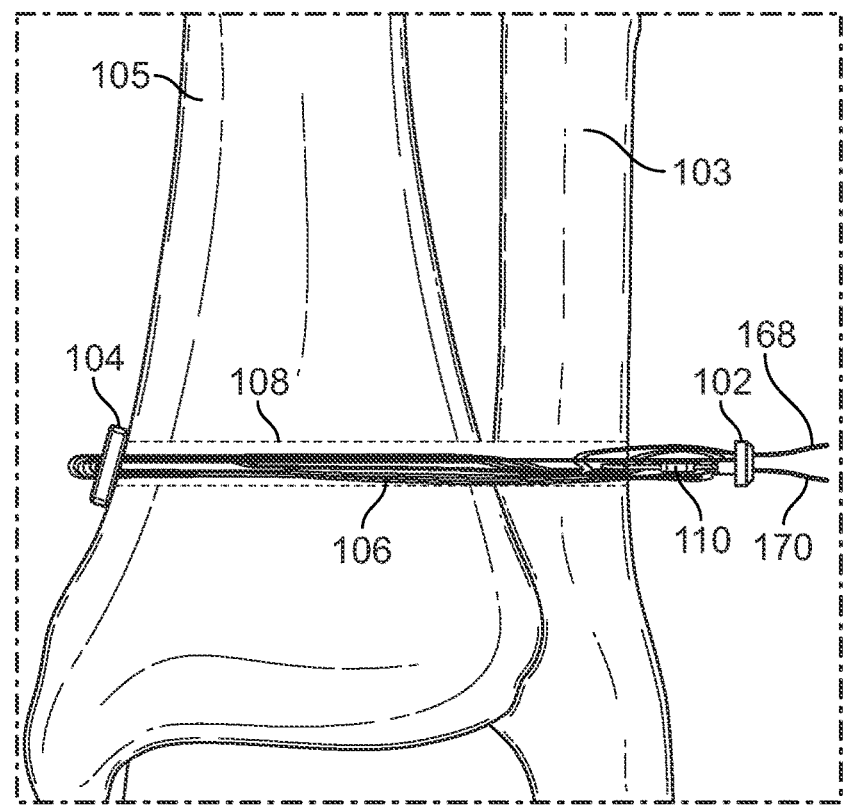
FIG. 17 is a side elevational view of the surgical site of FIG. 15 showing the second button seated and abutting the far cortex of the tibia, with first and second ends of the suture extending from openings of the first button and the suture not under tension.

Referring to FIG. 17, the second button 104 is shown having been advanced through the bone bore 108 and flipped from the flat configuration, so the distal surface 152 of the second button 104 is seated against and abutting the medial cortex of the tibia 105. At this step, the suture 106 and the first and second buttons 102, 104 are not yet held in tension, and the first button 102 is not yet in contact with the near cortex of the fibula 103. Once the second button 104 is secured against the medial cortex, the device 100 may be tensioned as shown in FIG. 18 to tie the first button 102 to the second button 104 and thereby tie bone segments 103, 105, the suture in this position shown cinched between the locking member 110 and locking loop 112.

Figure 18:
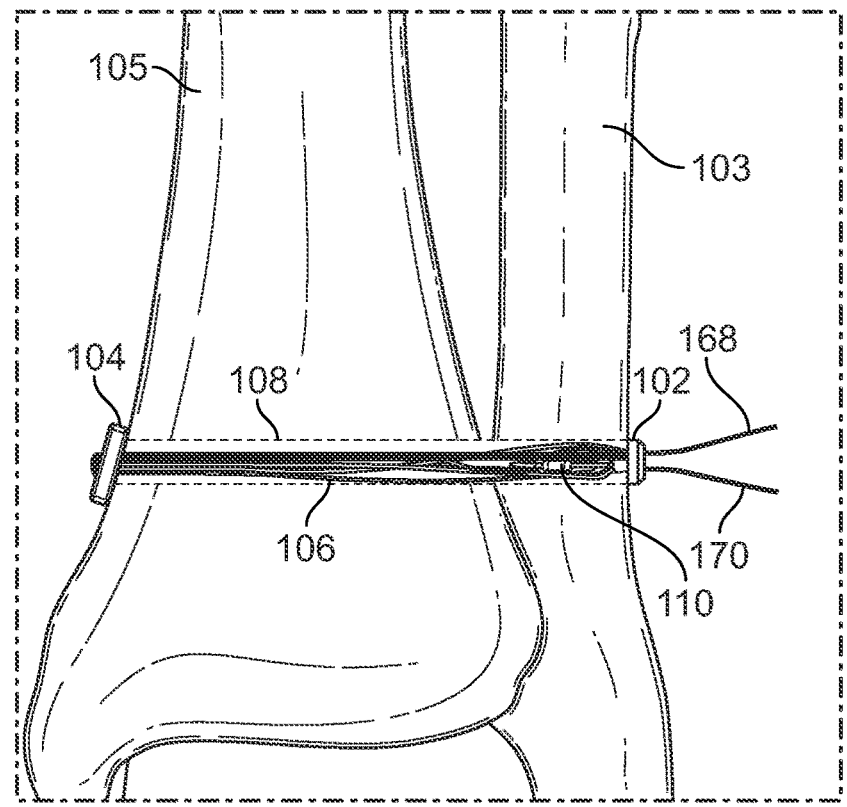
FIG. 18 is a side elevational view of the surgical site of FIG. 15 showing the suture under tension such that the first button is seated against the near cortex of the fibula and wherein the first button is tied to the second button by the suture thereby tying the fibula to the tibia.
Figure 19:
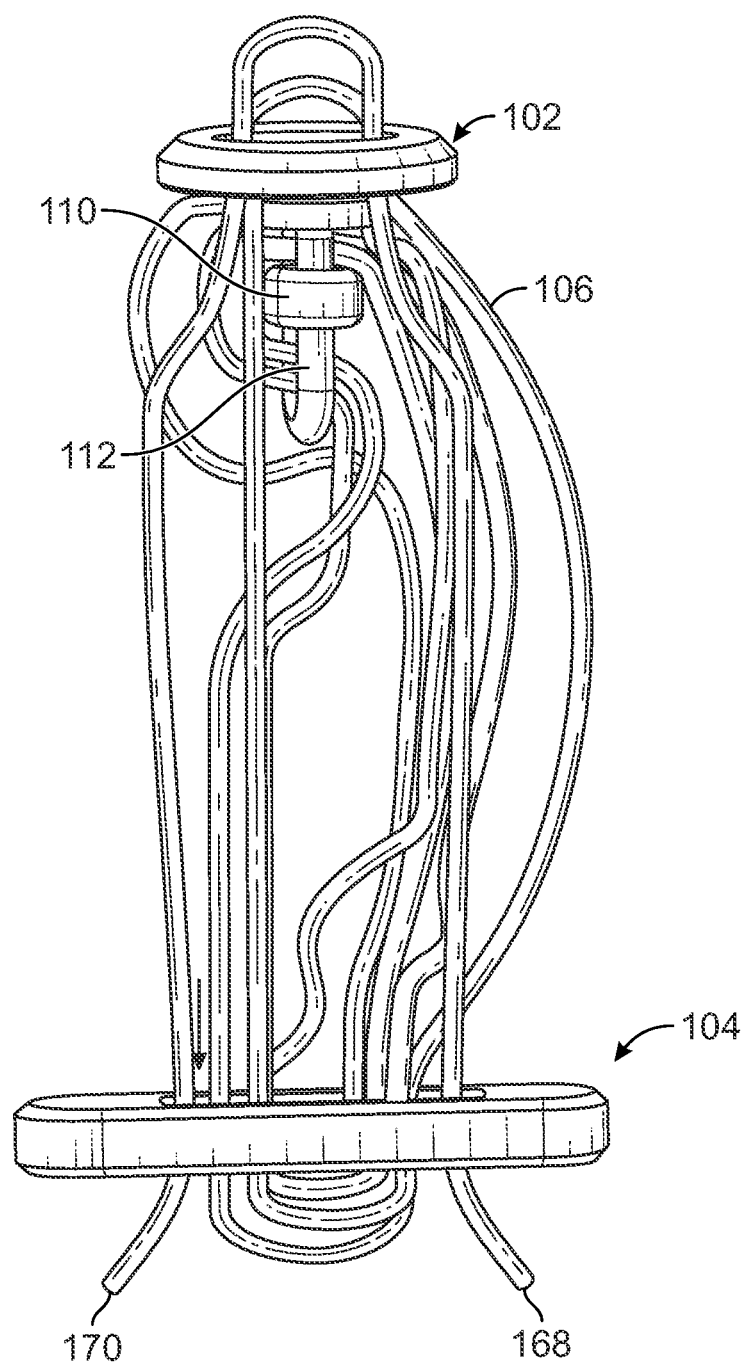
FIG. 19 is a perspective view of an alternative orthopedic stabilization device.

In FIG. 18, tension has been applied to the orthopedic stabilization device 100. As described above with respect to FIG. 12, a loop of the suture 106 extending around the locking member 110 will pull the locking member 110 in an axial direction such that the suture 106 will be cinched and frictionally retained between the locking member 110 and the locking loop 112. So configured, the orthopedic stabilization device 100 is inhibited from loosening once in the tensioned state due to the frictional retainment of the suture 106 between the locking member 110 and the locking loop 112. Additionally, as indicated above, the first and second ends 168, 170 are not required to be knotted once tensioned. In alternative embodiments, as shown in FIG. 19, the first and second ends 168, 170 of the suture 106 may extend from the distal surface 152 of the second button 104 such that the device 100 may be tensioned on the medial side of the bone segment (e.g., the tibia 105 in FIGS. 15-18) upon installation therein. To assemble this embodiment, the entering pass of the suture 106 may be made through the first opening 156 of the second button 104, through the second opening 124 of the first button 102, and over the first intermediate area 126. Thereafter, the suture 106 may be advanced through the device 100 in a manner generally not unlike the steps shown in FIGS. 14A-14E, and the suture 106 may exit the second opening 158 of the second button 104.

In either case, it is contemplated that the buttons and suture will be assembled by the manufacturer and not by the surgeon or hospital staff. It is contemplated in some embodiments that the buttons and suture may be provided unassembled, for surgeons that have a preference as to the configuration of the device.

Figure 20:
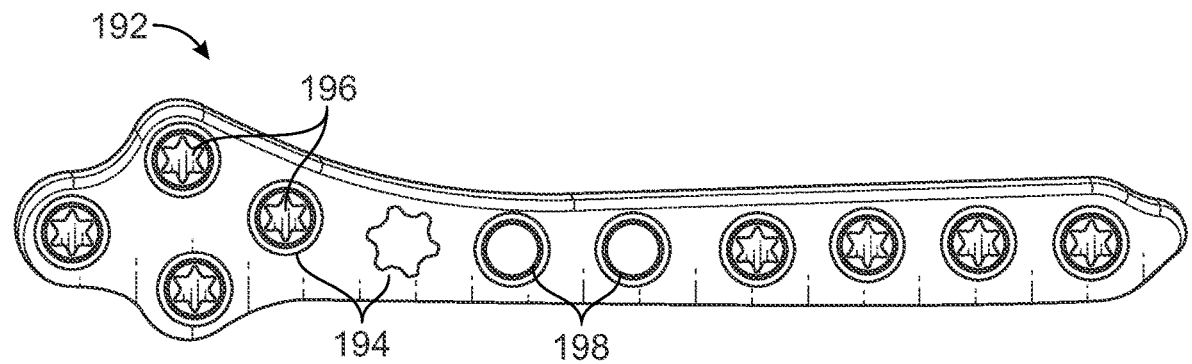
FIG. 20 is a perspective view of a bone plate having an opening sized to receive a first button of the orthopedic stabilization device of FIG. 1.

In other forms, the orthopedic stabilization device 100 may be used in connection with a bone plate (e.g., bone plate 192 shown in FIG. 20) such that the bone plate is positioned between the first button 102 and the surface of the bone. For example, such a bone plate may be used to repair a fracture, ligament, or joint. Referring to FIG. 20, an exemplary lateral fibula bone plate 192 is shown including a plurality of openings 194 sized to receive bone screws 196 therethrough to secure the bone plate 192 to a portion of bone. The orthopedic stabilization device 100 may be used in connection with bone plates of a variety of shapes, sizes, and having differing numbers of openings 194. In some embodiments, the openings 194 may be specifically sized to seat the first button 102 thereon. For example, openings 198 shown in FIG. 19 are configured to at least partially receive the first button 102 such that the first button 102 may be seated therein once the device 100 has been tensioned. In some forms, the bone plate 192 may include two or more openings 198 such that multiple orthopedic stabilization devices may be installed to improve the compressive force or otherwise promote tissue healing or repair.

Figure 21:
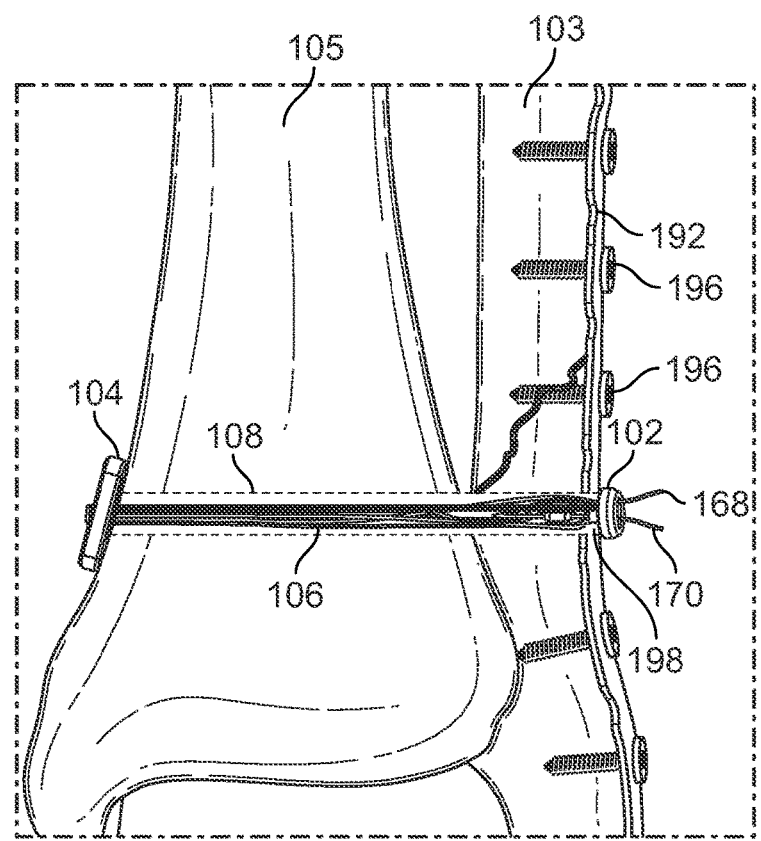
FIG. 21 is a side elevational of a surgical site where the bone plate of FIG. 20 and the orthopedic stabilization device of FIG. 1 are installed in a bone segment of a patient.

As shown in FIG. 21, the bone plate 192 of FIG. 20 has been positioned proximate the fibula 103 and screwed into place via bone screws 196 to secure the plate 192 thereto, preferably after a fracture shown in the fibula 103 has been reduced. Thereafter, a bore 108 is drilled through the fibula 103 and tibia 105 as hereinbefore discussed, and the orthopedic stabilization device 100 may thereafter be installed generally as described above.

Figure 22:
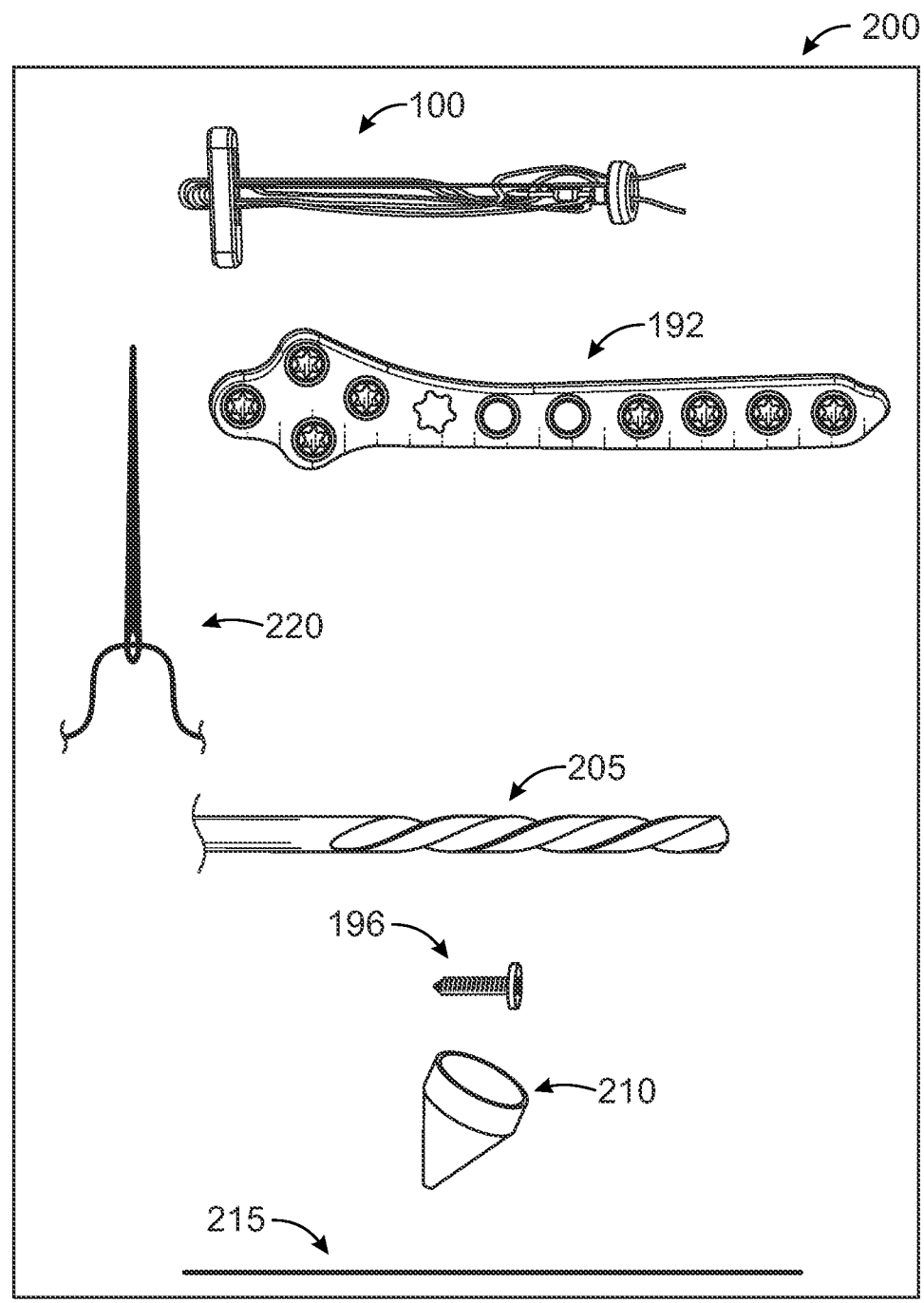
FIG. 22 shows an exemplary kit including an orthopedic stabilization device, a drill bit, a drill guide, and a passing device, among other optional components.

As shown in FIG. 22, a kit 200 may be provided including a number of components, such as the orthopedic stabilization device 100 (or another variant of the orthopedic stabilization device as described herein) and one or more of the other components shown, including a drill bit 205, a drill guide 210, a guide wire 215, a passing device 220, a bone plate, a bone screw 196, and any other suitable component. It is especially contemplated that the kit will include at least the orthopedic stabilization device, drill bit, and drill guide, and optionally a guide wire. The drill bit 205 may be provided in a variety of sizes depending on a desired size of the bore. Additionally, the drill guide 215 may be provided to inhibit irritation of surrounding tissue while, for example, a bore is being drilled into the one or more bone segments by the drill bit 205. The kit may be provided in the form of a sealed package containing the above-enumerated components. Variants of the kits including different components and different embodiments of the orthopedic stabilization device provided herein could be provided for different procedural indications. For example, a kit may be provided including an embodiment of the orthopedic stabilization device omitting the second button 104 such that the suture 106 may be coupled to a portion of tissue or another structure and tensioned between the tissue or structure and the first button 102.

As described above, the passing device 220 may be coupled to the orthopedic stabilization device 100 to shuttle the second button 104 and suture 106 through the bore drilled via the drill bit 205 such that the second button 104 may be positioned proximate the far cortex of the bone. In some forms, the passing device 220 may be needle-like and coupled to the second button 104 via a portion of string or suture for pulling the second button 104 and suture 106 looped therearound. In other forms, the passing device 220 may include an insertion tool such that the tool may push or carry the second button 104 through the bore and dispose the second button 104 on the far cortex of the bone, such that an incision near the far cortex may not be required.

It is thus seen that an orthopedic stabilization device, kit, and method can be provided in accordance with the foregoing teachings.

Uses of singular terms such as "a," "an," are intended to cover both the singular and the plural, unless otherwise indicated herein or clearly contradicted by context. The terms "comprising," "having," "including," and "containing" are to be construed as open-ended terms. Any description of certain embodiments as "preferred" embodiments, and other recitation of embodiments, features, or ranges as being preferred, or suggestion that such are preferred, is not deemed to be limiting. The invention is deemed to encompass embodiments that are presently deemed to be less preferred and that may be described herein as such. All methods described herein can be performed in any suitable order unless otherwise indicated herein or otherwise clearly contradicted by context. The use of any and all examples, or exemplary language (e.g., "such as") provided herein, is intended to illuminate the invention and does not pose a limitation on the scope of the invention. Any statement herein as to the nature or benefits of the invention or of the preferred embodiments is not intended to be limiting. This invention includes all modifications and equivalents of the subject matter recited herein as permitted by applicable law. Moreover, any combination of the above-described elements in all possible variations thereof is encompassed by the invention unless otherwise indicated herein or otherwise clearly contradicted by context. No unclaimed language should be deemed to limit the invention in scope. Any statements or suggestions herein that certain features constitute a component of the claimed invention are not intended to be limiting unless reflected in the appended claims. Neither the marking of the patent number on any product nor the identification of the patent number in connection with any service should be deemed a representation that all embodiments described herein are incorporated into such product or service.

What is claimed is:

1. A bone stabilization method comprising:
   surgically exposing one or more bone segments of a patient, at least one of the bone segments having a near cortex surface and at least one of the bone segments having a far cortex surface;
   drilling a hole through the one or more bone segments;
   providing an orthopedic stabilization device;
   wherein the orthopedic stabilization device comprises:
   a first button having a base portion and a locking loop, the base portion having a proximal surface, a distal surface, and one or more openings extending therethrough, the locking loop extending from a distal surface of the base portion in an axial direction;
   a locking member having an aperture sized to receive the locking loop such that the locking member is slidably engageable therewith;
   a second button having one or more openings extending therethrough; and
   a suture disposed between the first button and the second button, wherein said locking loop and said locking member are sized such that a portion of said suture is frictionally retainable between said locking member and said locking loop to thereby tie said first button to said second button;
   advancing the second button and suture through the hole such that the second button exits the hole proximate the far cortex surface; and
   tensioning the suture such that the first button is positioned proximate the near cortex surface and is tied to the second button, and wherein a portion of the suture is frictionally retained between the locking member and locking loop.

2. The method of claim 1, wherein at least a portion of the suture extends through the locking loop of the orthopedic stabilization device superior the locking member in the axial direction and at least a portion of the suture extends through the locking loop inferior the locking member in the axial direction.

3. The method of claim 1, wherein the base portion of the first button of the orthopedic stabilization device includes first and second openings extending therethrough and a first intermediate area extending between the first and second openings of the first button, and wherein the second button has first and second openings extending therethrough and a second intermediate area extending between the first and second openings of the second button.

4. The method of claim 3, wherein a portion of the suture extends through the first and second openings of the second button of the orthopedic stabilization device to thereby form a first loop around said second intermediate area;
wherein a portion of the suture extends through the locking loop, around said locking member, and through the locking loop;
wherein a portion of the suture extends through the first and second openings of the first button to thereby form a loop around said first button intermediate area;
whereby when tension is applied to the suture, the locking member is biased in the inferior direction to frictionally retain the suture between the locking member and the locking loop.

5. The method of claim 4,
wherein a first end of the suture is disposed proximally of said first button and said suture extends distally through the first opening of the first button of the orthopedic stabilization device;
wherein a portion of the suture extends through the first and second openings of the second button to thereby form a first loop around said second intermediate area;
wherein a portion of the suture extends through the locking loop, around said locking member, and through the locking loop;
wherein a portion of the suture extends through the first and second openings of the first button to thereby form a loop around said first intermediate area; and
wherein a second end of the suture extends outwardly through a second opening of the first button.

6. The method of claim 5, where the suture of the orthopedic stabilization device:
makes an entering pass through the first opening of said first button;
makes a first pass around said second intermediate portion;
makes a first pass through said locking loop and around said locking member;
makes a second pass around said second intermediate area;
makes a pass around said first intermediate area;
makes a third pass around said second intermediate area;
makes a second pass through said locking loop and around said locking member;
makes a fourth pass around said second intermediate area; and
makes an exiting pass through a second opening of said first button.

7. The method of claim 5, where the suture of the orthopedic stabilization device:
makes an entering pass through a first opening of said second button;
makes a first pass around said first intermediate portion;
makes a first pass around said second intermediate portion;
makes a first pass through said locking loop and around said locking member;
makes a second pass around said second intermediate area;
makes a second pass around said first intermediate area;
makes a third pass around said second intermediate area;
makes a second pass through said locking loop and around said locking member;
makes a fourth pass around said second intermediate area;
makes a third pass around said first intermediate area; and
makes an exiting pass through a second opening of said second button.

8. The method of claim 1, wherein the one or more openings of the first button of the orthopedic stabilization device are sized to frictionally retain the suture to inhibit relative movement of the suture and the first button.

9. The method of claim 1, wherein the first and second buttons of the orthopedic stabilization device each independently comprise one or more of a titanium material, a polyether ether ketone material, and a poly-L-lactic acid material.

10. The method of claim 1, further comprising:
providing a bone plate proximate the near cortex surface, the bone plate including at least one aperture sized to at least partially receive and seat the first button;
fastening the bone plate to the near cortex surface via one or more bone screws; and
seating the first button in the opening of the bone plate upon the suture being tensioned.

11. The method of claim 1, further comprising:
reducing a fracture of the one or more bone segments before drilling the hole through the one or more bone segments.

12. An orthopedic stabilization device comprising:
a first button having a base portion and a locking loop, the base portion having a proximal surface, a distal surface, and first and second openings extending between the proximal surface and the distal surface, the locking loop extending from a distal surface of the base portion in an axial direction;
a locking member having an aperture sized to receive the locking loop such that the locking member is slidably engageable therewith;
a second button having one or more openings extending therethrough; and
a suture disposed between the first button and the second button, wherein said locking loop and said locking member are sized such that a portion of said suture is frictionally retainable between said locking member and said locking loop to thereby tie said first button to said second button, a portion of the suture passing between the proximal surface and the distal surface of the first button through each of said first and second openings.

13. A kit comprising:
the orthopedic stabilization device of claim 12;
a drill bit;
a drill guide; and
a passing device.

14. The kit of claim 13, further comprising:
a bone plate including at least one aperture sized to at least partially receive and seat the first button.

15. The kit of claim 14, further comprising:
a bone screw, wherein said bone plate includes at least a second aperture for receiving said bone screw.

16. The orthopedic stabilization device of claim 12, wherein at least a portion of the suture extends through the locking loop superior the locking member in the axial direction and at least a portion of the suture extends through the locking loop inferior the locking member in the axial direction.

17. An orthopedic stabilization device according to claim 12, wherein the base portion of the first button includes a first intermediate area extending between the first and second openings of the first button, and wherein the second button has first and second openings extending therethrough and a second intermediate area extending between the first and second openings of the second button, wherein a portion of the suture extends through the first and second openings of the second button to thereby form a first loop around said second intermediate area;

wherein a portion of the suture extends through the locking loop, around said locking member, and through the locking loop;

wherein a portion of the suture extends through the first and second openings of the first button to thereby form a loop around said first button intermediate area;

whereby when tension is applied to the suture, the locking member is biased in the inferior direction to frictionally retain the suture between the locking member and the locking loop, wherein a first end of the suture is disposed proximally of said first button and said suture extends distally through the first opening of the first button;

wherein a portion of the suture extends through the first and second openings of the second button to thereby form a first loop around said second intermediate area;

wherein a portion of the suture extends through the locking loop, around said locking member, and through the locking loop;

wherein a portion of the suture extends through the first and second openings of the first button to thereby form a loop around said first intermediate area; and wherein a second end of the suture extends outwardly through the second opening of the first button.

18. An orthopedic stabilization according to claim 17, where the suture:

makes an entering pass through the first opening of said first button;

makes a first pass around said second intermediate portion;

makes a first pass through said locking loop and around said locking member;

makes a second pass around said second intermediate area;

makes a pass around said first intermediate area;

makes a third pass around said second intermediate area;

makes a second pass through said locking loop and around said locking member;

makes a fourth pass around said second intermediate area; and makes an exiting pass through the second opening of said first button.

19. An orthopedic stabilization device according to claim 17, where the suture:

makes an entering pass through a first opening of said second button;

makes a first pass around said first intermediate portion;

makes a first pass around said second intermediate portion;

makes a first pass through said locking loop and around said locking member;

makes a second pass around said second intermediate area;

makes a second pass around said first intermediate area;

makes a third pass around said second intermediate area;

makes a second pass through said locking loop and around said locking member;

makes a fourth pass around said second intermediate area;

makes a third pass around said first intermediate area; and makes an exiting pass through a second opening of said second button.

20. The device of claim 12, wherein said first and second openings of said first button are sized to frictionally retain the suture to inhibit relative movement of the suture and the first button.

21. The device of claim 12, wherein the first and second buttons each independently comprise one or more of a titanium material, a polyether ether ketone material, and a poly-L-lactic acid material.

\* \* \* \* \*